United States Patent [19]

Ebetino et al.

[11] Patent Number: 5,137,880
[45] Date of Patent: Aug. 11, 1992

[54] BICYCLIC DIPHOSPHONATE COMPOUNDS, PHARMACEUTICAL COMPOSITIONS, AND METHODS FOR TREATING ABNORMAL CALCIUM AND PHOSPHATE METABOLISM

[75] Inventors: Frank H. Ebetino; Kent W. Buckingham; Jocelyn E. McOsker, all of Norwich, N.Y.

[73] Assignee: Norwich Eaton Pharmaceuticals, Inc., Norwich, N.Y.

[21] Appl. No.: 407,848

[22] Filed: Sep. 14, 1989

Related U.S. Application Data

[62] Division of Ser. No. 945,069, Dec. 19, 1986, Pat. No. 4,868,164.

[51] Int. Cl.$^5$ .................. C07F 9/65; A61K 31/675
[52] U.S. Cl. ........................ 514/80; 514/89; 540/476; 546/23
[58] Field of Search ............... 546/23; 514/80

[56] References Cited

U.S. PATENT DOCUMENTS

| | | | |
|---|---|---|---|
| 3,553,314 | 1/1971 | Francis | 424/49 |
| 3,683,080 | 8/1972 | Francis | 514/107 |
| 3,846,420 | 11/1974 | Wollmann et al. | 544/157 |
| 3,899,496 | 8/1975 | Schindler et al. | 546/22 |
| 3,941,772 | 3/1976 | Ploger et al. | 546/6 |
| 3,957,160 | 5/1976 | Ploger et al. | 210/58 |
| 3,960,888 | 6/1976 | Ploger et al. | 548/412 A |
| 3,979,385 | 9/1976 | Wollman et al. | 544/157 |
| 3,988,443 | 10/1976 | Ploger et al. | 514/79 |
| 4,117,090 | 9/1978 | Ploger | 423/268 |
| 4,267,108 | 5/1981 | Blum et al. | 548/413 |
| 4,687,767 | 8/1987 | Bosies et al. | 514/89 |
| 4,687,768 | 8/1987 | Benedict et al. | 514/102 |
| 4,719,203 | 1/1988 | Bosies et al. | 514/108 |

FOREIGN PATENT DOCUMENTS

| | | | |
|---|---|---|---|
| 8781451 | 5/1988 | Australia | 34/548 |
| 8781453 | 5/1988 | Australia | 548/112 |
| 8781692 | 6/1988 | Australia | 546/23 |
| 1002300 | 3/1983 | U.S.S.R. | |

OTHER PUBLICATIONS

Izv. Akad. Nauk SSSR, Ser. Khim (12)2802 (1983) (Chemical Abstract 100:121244).

Primary Examiner—Alan L. Rotman
Attorney, Agent, or Firm—Kim William Zerby; Karen F. Clark; David L. Suter

[57] ABSTRACT

The present invention relates to novel compounds having nitrogen-containing, saturated bicyclic cylopentane-fused rings which are geminally disubstituted with phosphonate groups. Most preferred compounds of the present invention have the general structure:

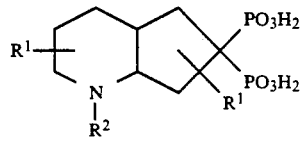

The present invention further relates to pharmaceutical compositions containing these novel compounds. Finally, this invention relates to methods for treating or preventing diseases characterized by abnormal calcium and phosphate metabolism by utilizing a compound or pharmaceutical composition of the present invention.

15 Claims, No Drawings

BICYCLIC DIPHOSPHONATE COMPOUNDS, PHARMACEUTICAL COMPOSITIONS, AND METHODS FOR TREATING ABNORMAL CALCIUM AND PHOSPHATE METABOLISM

This is a divisional of application Ser. No. 945,069 filed on Dec. 19, 1986, issued as U.S. Pat. No. 4,868,164 on Sep. 19, 1989.

BACKGROUND OF THE INVENTION

The present invention relates to novel compounds which are nitrogen-containing, saturated bicyclic cyclopentane-fused diphosphonate compounds, especially substituted or unsubstituted octahydro pyrindine diphosphonate derivatives. The present invention further relates to pharmaceutical compositions which contain the novel compounds of the present invention. Finally, the present invention relates to a method for treating or preventing diseases characterized by abnormal calcium and phosphate metabolism by utilizing a compound or pharmaceutical composition of the present invention.

A number of pathological conditions which can afflict humans and lower animals involve abnormal calcium and phosphate metabolism. Such conditions may be divided into two broad categories:

(1) Conditions which are characterized by anomolous mobilization of calcium and phosphate leading to general or specific bone loss, or excessively high calcium and phosphate levels in the fluids of the body, such as osteoporosis and Paget's disease. Such conditions are sometimes referred to herein as pathological hard tissue demineralizations.

(2) Conditions which cause or result from deposition of calcium and phosphate anomolously in the body, such as arthritis. These conditions are sometimes referred to herein as pathological calcifications.

A variety of polyphosphonic acid derivatives have been proposed for use in the treatment and prophylaxis of diseases involving abnormal calcium and phosphate metabolism. For example, U.S. Pat. No. 3,683,080, issued Aug. 8, 1972 to Francis, discloses compositions containing polyphosphonates, in particular diphosphonates, and their use in inhibiting anomolous deposition and mobilization of calcium phosphate in animal tissue; U.S. Pat. No. 4,230,700, issued Oct. 28, 1980 to Francis, discloses composition containing certain phosphonate compounds (e.g. cycloalkyl-substituted hydroxyethane diphosphonates) in combination with vitamin D-like compounds useful in inhibiting mobilization of calcium phosphate in animal tissue; U.S. Pat. No. 3,988,443, issued Oct. 26, 1976 to Ploger et al, discloses azacycloalkane-2,2-diphosphonate compound said to be useful as sequestering agents and as agents in the treatment of diseases related to the abnormal deposition or dissolution of difficulty soluble calcium salts in the animal body; and European Patent Application Publication No. 189,662, published Aug. 6, 1986, which discloses various specific cyclic diphosphonate compounds said to be useful as sequestering agents or as agents in the treatment of diseases characterized by abnormal calcium and phosphate metabolism. The disclosures of all these patents and applications are incorporated herein by reference in their entirety.

In spite of this and much other research into the use of diphosphonates to treat bone-metabolism diseases, there continues to be a need for new bone-active agents. The object of the present invention is therefore to provide new bone-active diphosphonate compounds having relatively high potency for inhibiting bone resorption. Furthermore, an object of the present invention is to provide new bone-active diphosphonate compounds with low toxicity and favorable therapeutic indices. It is a further object of the present invention to provide pharmaceutical compositions useful for the treatment and prophylaxis of abnormal calcium and phosphate metabolism. In addition, it is an object of the present invention to provide methods for treating or preventing diseases characterized by abnormal calcium and phosphate metabolism in humans or lower animals.

These and other objects of the present invention will become apparent from the detailed disclosure of the present invention provided hereinafter.

SUMMARY OF THE INVENTION

The present invention relates to compounds having nitrogen-containing, saturated bicyclic cyclopentane-fused rings which are geminally disubstituted with phosphonate groups. Preferred are substituted or unsubstituted octahydro pyrindine diphosphonate compounds, especially substituted or unsubstituted octahydro 1-pyrindine-6,6-diphosphonic acid compounds, and the pharmaceutically-acceptable salts and esters thereof.

The present invention further relates to pharmaceutical compositions containing a safe and effective amount of a compound of the present invention, and a pharmaceutically-acceptable carrier. Finally, the present invention relates to methods for treating or preventing pathological conditions characterized by abnormal calcium and phosphate metabolism in humans or lower animals. This method comprises administering to a human or lower animal in need of such treatment a safe and effective amount of a compound or composition of the present invention.

DETAILED DESCRIPTION OF THE INVENTION

Nitrogen-containing, saturated bicyclic cyclopentane ring-containing diphosphonate compounds:

The compounds of the present invention fall within the class of saturated cyclopentane compounds which are geminally disubstituted with phosphonic acids, salts or esters, and which are fused with a nitrogen-containing, saturated ring to thereby form a bicyclic ring structure. This nitrogen-containing, saturated bicyclic cyclopentane diphosphonate ring structure has the general structure:

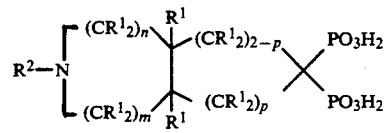

wherein m and n and m+n are integers from about 0 to about 5 (preferred is m+n=3, and most preferred is m=0 and n=3); p is an integer from 0 to 2 (preferred is p=1); each $R^1$ is independently selected from the group consisting of hydrogen, alkyl having from about 1 to about 6 carbon atoms, $-OR^3$, $-CO_2R^3$, $-O_2CR^3$, $-NR^3{}_2$, $-N(R^3)C(O)R^3$, $-C(O)N(R^3)_2$, halogen, $-C(O)R^3$, phenyl, benzyl, nitro, and combinations thereof; $R^2$ is selected from the group consisting of hydrogen, alkyl having from about 1 to about 6 carbon atoms, $R^3C(O)$—, phenyl, and benzyl; each $R^3$ is independently selected from the group consisting of hydrogen and alkyl having from about 1 to about 3 carbon atoms (preferred $R^3$ are hydrogen, methyl, and ethyl); and the pharmaceutically-acceptable salts and esters thereof.

Preferred $R^1$ is hydrogen, alkyl having from about 1 to about 6 carbon atoms, —$NR^3_2$, and hydroxy; and preferred $R^2$ is hydrogen, alkyl having from about 1 to about 6 carbon atoms, and $R^3C(O)$—. More preferred $R^1$ is hydrogen, methyl, ethyl, —$NH_2$, and hydroxy; and most preferred is $R^1$ being hydrogen. More preferred $R^2$ is hydrogen, methyl, and ethyl; and most preferred is $R^2$ being hydrogen.

The term "alkyl", as used herein, means carbon-containing chains which may be straight or branched, and which may be saturated, monounsaturated, or polyunsaturated. Preferred are saturated alkyl groups. Further, while it is preferred that the alkyl, phenyl, and benzyl substituent groups described hereinbefore be unsubstituted, these groups themselves may be substituted with a variety of substituents (e.g.: methyl, ethyl, propyl, substituted or unsubstituted amino, carboxy, hydroxy, methoxy, ethoxy, halogen) and still be considered within the scope of the present invention.

Preferred compounds of the present invention are substituted or unsubstituted octahydro pyrindine diphosphonic acids, and the pharmaceutically-acceptable salts and esters thereof, having the general structures:

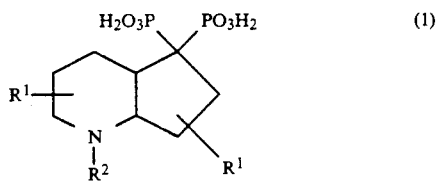
(1)

referred to herein as "unsubstituted or substituted octahydro-1-pyrindine-5,5-diphosphonic acids";

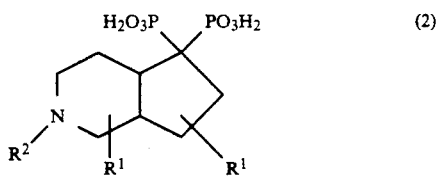
(2)

referred to herein as "unsubstituted or substituted octahydro-2-pyrindine-5,5-diphosphonic acids";

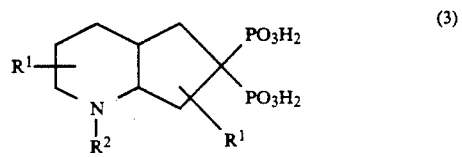
(3)

referred to herein as "unsubstituted or substituted octahydro-1-pyrindine-6,6-diphosphonic acids";

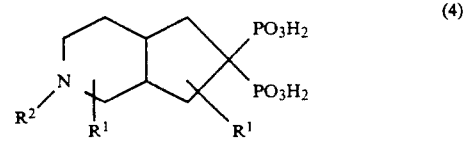
(4)

referred to herein as "unsubstituted or substituted octahydro-2-pyrindine-6,6-diphosphonic acids";

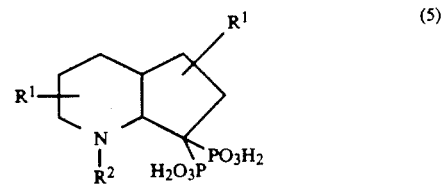
(5)

referred to herein as "unsubstituted or substituted octahydro-1-pyrindine-7,7-diphosphonic acids"; and

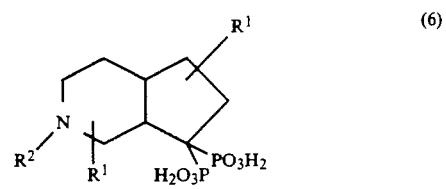
(6)

referred to herein as "unsubstituted or substituted octahydro-2-pyrindine-7,7-diphosphonic acids".

More preferred compounds of the present invention are substituted or unsubstituted octahydro-1-pyrindine-6,6-diphosphonic acids, and the pharmaceutically-acceptable salts and esters thereof; and substituted or unsubstituted octahydro-2-pyrindine-6,6-diphosphonic acids, and the pharmaceutically-acceptable salts and esters thereof. Most preferred compounds of the present invention are substituted or unsubstituted octahydro-1-pyrindine6,6-diphosphonic acids, and the pharmaceutically-acceptable salts and esters thereof.

Specific examples of compounds of the present invention include:
octahydro-1-pyrindine-5,5-diphosphonic acid;
octahydro-2-pyrindine-5,5-diphosphonic acid;
octahydro-1-pyrindine-6,6-diphosphonic acid;
octahydro-2-pyrindine-6,6-diphosphonic acid;
octahydro-1-pyrindine-7,7-diphosphonic acid;
octahydro-2-pyrindine-7,7-diphosphonic acid;
2-methyl-octahydro-1-pyrindine-5,5-diphosphonic acid;
1,3-diethyl-octahydro-2-pyrindine-5,5-diphosphonic acid;
7-hydroxy-octahydro-1-pyrindine-6,6-diphosphonic acid;
4-methoxy-octahydro-2-pyrindine-6,6-diphosphonic acid;
5-vinyl-octahydro-1-pyrindine-7,7-diphosphonic acid;
1-(dimethylamino)-octahydro-2-pyrindine-7,7-diphosphonic acid;
N-acetyl-octahydro-2-pyrindine-6,6-diphosphonic acid;
N-benzyl-octahydro-1-pyrindine-5,5-diphosphonic acid;
N-(p-methoxyphenyl)-octahydro-2-pyrindine-7,7-diphosphonic acid;
2-(3,4-dichlorophenyl)-octahydro-1-pyrindine-7,7-diphosphonic acid;

2-(p-dimethylaminophenyl)-octahydro-1-pyrindine-7,7-diphosphonic acid;
4-chloro-octahydro-1-pyrindine-6,6-diphosphonic acid;
4-amino-octahydro-1-pyrindine-6,6-diphosphonic acid;
7-carboxy-octahydro-1-pyrindine-6,6-diphosphonic acid;
5-carboxy(methyl ester)-octahydro-1-pyrindine-6,6-diphosphonic acid;
4-hydroxy-octahydro-2-pyrindine-6,6-diphosphonic acid, propanoate ester;
4-(N,N-dimethylamino)-octahydro-1-pyrindine-6,6-diphosphonic acid;
5-(N-acetamido)-octahydro-1-pyrindine-7,7-diphosphonic acid;
7-(ethylketone)-octahydro-2-pyrindine-5,5-diphosphonic acid; and
4-nitro-octahydro-1-pyrindine-6,6-diphosphonic acid;
and the pharmaceutically-acceptable salts and esters thereof.

Preferred compounds of the present invention are:
octahydro-1-pyrindine-5,5-diphosphonic acid;
octahydro-2-pyrindine-5,5-diphosphonic acid;
octahydro-1-pyrindine-6,6-diphosphonic acid;
octahydro-2-pyrindine-6,6-diphosphonic acid;
octahydro-1-pyrindine-7,7-diphosphonic acid;
octahydro-2-pyrindine-7,7-diphosphonic acid;
N-methyl-octahydro-1-pyrindine-6,6-diphosphonic acid; and
4-amino-octahydro-1-pyrindine-6,6-diphosphonic acid;
and the pharmaceutically-acceptable salts and esters thereof. The most preferred compound of the present invention is octahydro-1-pyrindine-6,6-diphosphonic acid, and the pharmaceutically-acceptable salts and esters thereof.

It is further desirable that the compounds of the present invention have a "cis" ring juncture. Therefore, it is preferred, for example, that octahydro-1-pyrindine-6,6-diphosphonate have the structure:

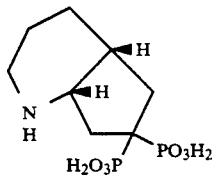

The term "pharmaceutically-acceptable salts and esters", as used herein, means hydrolyzable esters and salts of the diphosphonate compounds which have the same general pharmacological properties as the acid form from which they are derived, and which are acceptable from a toxicity viewpoint. Pharmaceutically-acceptable salts include alkali metals (e.g., sodium and potassium), alkaline earth metals (e.g., calcium and magnesium), non-toxic heavy metals (e.g., stanous and indium), and ammonium and low molecular weight substituted ammonium (e.g., mono-, di- and triethanolamine) salts. Preferred compounds are the sodium, potassium, and ammonium salts.

The compounds of the present invention have demonstrated significantly better bone anti-resorptive activity than art-known diphosphonate compounds such as ethane-1-hydroxy-1,1-diphosphonic acid ("EHDP"; disclosed in U.S. Pat. No. 3,683,080 to Francis, Issued Aug. 8, 1972) and azacyclopentane-2,2-diphosphonic acid (disclosed in U.S. Pat. No. 3,988,443 to Ploger et al., Issued Oct. 26, 1976). More surprisingly, the compounds of the present invention have demonstrated significantly better bone anti-resorptive activity than compounds which have very similar chemical structures. For example, octahydro-1-pyrindine-6,6-diphosphonate of the present invention surprisingly is a much more potent bone resorption inhibiting agent (as demonstrated by test methods described more fully hereinafter in Example 6) than the following chemically very similar compounds (disclosed in European Patent Application Publication No. 189,662):

1) dihydro-1-pyrindine-6,6-diphosphonate, having the structure:

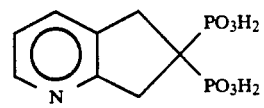

2) hexahydroindan-2,2-diphosphonate, having the structure:

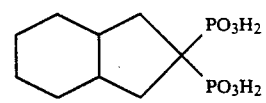

3) indan-2,2-diphosphonate, having the structure:

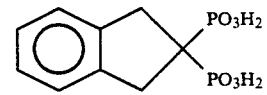

In addition, the compounds of the present invention have demonstrated very low toxicity, and therefore are believed to have very good therapeutic indices. Finally, at an effective dose for inhibition of bone resorption, the compounds of the present invention are expected to inhibit bone mineralization either very little or not at all.

In order to determine and assess pharmacological activity, testing of the diphosphonate compounds in animals is carried out using various assays known to those skilled in the art. Thus, the in vivo bone antiresorptive activity may be conveniently demonstrated using an assay designed to test the ability of these compounds to inhibit the resorption of bone, which bone resorption is characteristic of abnormal calcium and phosphate metabolism. Examples of such known tests include the thyroparathyroidectomized ("TPTX") rat model and the Schenk model. Another useful art-known test is the adjuvant arthristis test. Also useful is the in vitro hydroxyapatite crystal growth inhibition test. These and other appropriate tests for pharmacological activity are disclosed and/or referred to in Shinoda et al., *Calcified Tissue International*, 35, pp 87–99 (1983); Schenk et al., *Calcified Tissue Research* 11, pp 196–214 (1973); Russell et al., *Calcified Tissue Research*, 6, pp 183–196 (1970); Muhlbauer and Fleisch, *Mineral Electrolyte Metab.*, 5, pp 296–303 (1981); Nancollas et al., *Oral Biol.*, 15, 731 (1970); U.S. Pat. No. 3,683,080, to Francis, Issued Aug. 8, 1972; U.S. Pat. No. 4,134,969, to Schmidt-Dunker, Issued Jan. 16, 1979; and EPO Patent Application Publication No. 189,662, published Aug. 6, 1986; the disclosures of all these articles and patent specifications being incorporated herein by reference in their entirety. Certain of these tests for pharmacological activity are also described in more detail in the Examples provided hereinafter.

In addition to being useful for treating or preventing pathological conditions characterized by abnormal calcium or phosphate metabolism, the compounds of the present invention may have other uses. For example, the compounds of the present invention are believed to be useful as bone scanning agents after labeling with 99m-Technetium. In addition, the compounds of the present invention are useful as sequestering agents for polyvalent metal ions, particularly di- and tri-valent metal ions (e.g. calcium and magnesium). Thus, the compounds of the present invention are useful as builders in detergents and cleansers, or for treating water. They are also useful as stabilizers for percompounds. In addition, they may be useful in preventing the formation of tartar (i.e., calculus) and/or plaque on teeth. Finally, the compounds of the present invention may be useful as herbicides which are non-toxic to animals.

The diphosphonate compounds of the present invention are prepared from commercially-available materials. Synthesis techniques useful for the preparation of the present compounds are described, for example, in EPO Patent Application Publication No. 189,662 which is incorporated by reference in its entirety hereinbefore. Generally, the synthesis reaction may be carried out in the following way: In a first step, a methane diphosphonate ester, in solution, is converted to the corresponding carbanion. In a second step, to this reaction mixture is added a solution of hydrocarbon compound suitably activated for a double nucleophilic substitution. Finally, if necessary a third step is performed through which any unsaturation in the compound is saturated, usually by hydrogenation.

Typically, a solution of methane diphosphonate ester is added to a cold suspension of potassium hydride in an inert organic solvent, and the solution left to stir at room temperature. The suitably activated hydrocarbon is then added as a solution to the reaction mixture, and the entire mixture is heated to about 80° C. until completion. After the mixture is cooled, filtered, and concentrated, the concentrate is chromatographed on silica gel to obtain the desired ester. This ester is hydrolyzed by refluxing in HCl and the resulting material concentrated under vacuum. The residue is dissolved in $H_2O$ and treated with activated charcoal. Following filtration, the solution is concentrated, and the product is dried under vacuum. Finally, if necessary, the material is hydrogenated in solution over an appropriate catalyst and then purified. Representative procedures for synthesizing compounds of the present invention are provided in the Examples hereinafter.

Compounds of the present invention may comprise from about 0.1% to about 99.9% by weight of the pharmaceutical compositions of the present invention. Preferably the compounds of the present invention comprise from about 20% to about 80% by weight of the pharmaceutical compositions of the present invention.

Pharmaceutically-Acceptable Carrier

In addition to the nitrogen-containing, saturated bicyclic cyclopentane ring-containing diphosphonate compounds as described hereinbefore, the pharmaceutical compositions of the present invention essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the diphosphonate compounds, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of the substances which can serve as pharmaceutical carriers are sugars such as lactose, glucose and sucrose; starches such as corn starch and potato starch; cellulose and its derivatives, such as sodium carboxymethylcellulose, ethylcellulose, cellulose acetate; powdered tragacanth; malt; gelatin, talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; sugar; alginic acid; pyrogen-free water; istonic saline; and phosphate buffer solutions, as well as other non-toxic compatible substances used in pharmaceutical formulations. Wetting agents and lubricants such as sodium lauryl sulfate, as well as coloring agents, flavoring agents and preservatives, can also be present. Other compatible pharmaceutical additives and actives may be included in the pharmaceutically-acceptable carrier for use in the compositions of the present invention.

The choice of a pharmaceutically-acceptable carrier to be used in conjunction with the diphosphonate compound of the present invention is basically determined by the way the diphosphonate compound is to be administered. If the compound is to be injected, the preferred pharmaceutical carrier is sterile physiological saline, the pH of which has been adjusted to about 7.4. Suitable pharmaceutically-acceptable carriers for topical application include those suited for use in creams, gels, tapes and the like.

The preferred mode of administering the diphosphonate compound of the present invention is orally. The preferred unit dosage form is therefore tablets, capsules and the like, comprising a safe and effective amount of the diphosphonate compound of the present invention. Preferably, the compositions comprise from about 1 mg P to about 600 mg P of a diphosphonate compound of the present invention. Pharmaceutically-acceptable carriers suitable for the preparation of unit dosage forms for oral administration are well known in the art. Their selection will depend on secondary considerations like taste, cost, and shelf stability, which are not critical for the purposes of the present invention, and can be made without difficulty by a person skilled in the art.

The term "mg P", as used herein, means the weight of the phosphorous atoms present in an amount of a diphosphonic acid compound of the present invention. This unit is used to standardize the amount of the diphosphonic acid compounds of the present invention to be used in the pharmaceutical compositions and methods of the present inventions. For example, octahydro-1-pyrindine-6,6-diphosphonic acid has a molecular weight of 285 g/mole, of which 21.8% (62 g/mole) is due to the two phosphorous atoms present in this molecule. One milligram of this compound is therefore calculated to have 0.218 mg P (1 mg×21.8%). Thus, to prepare a pharmaceutical composition containing 0.218 mg P of this compound, the composition should contain 1 mg of the compound; and to dose 0.218 mg P/kg of this compound to a 50 kg patient, the patient would be dosed with 50 mg of this compound.

The pharmaceutically-acceptable carrier employed in conjunction with the diphosphonate compounds of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, and preferably from about 20% to about 80%.

Method for Treating or Preventing Diseases Characterized by Abnormal Calcium and Phosphate Metabolism Another aspect of the present invention is methods for treating or preventing diseases characterized by abnormal calcium and phosphate metabolism. Such methods comprise administering to a human or lower animal in need of such treatment a safe and effective amount of a diphosphonate compound of the present invention.

The preferred mode of administration is oral, but other known methods of administration are contemplated as well, e.g., dermatomucosally (for example, dermally, rectally and the like) and parenterally (for example, by subcutaneous injection, intramuscular injection, intra-articular injection, intravenous injection and the like). Inhalation is also included. Thus, specific modes of administration include, without limitation, oral, transdermal, mucosal, sublingual, intramuscular, intravenous, intraperitoneal, and subcutaneous administration, as well as topical application.

The term "abnormal calcium and phosphate metabolism", as used herein, means (1) conditions which are characterized by anomalous mobilization of calcium and phosphate leading to general or specific bone loss, or excessively high calcium and phosphate levels in the fluids of the body; and (2) conditions which cause or result from deposition of calcium and phosphate anomalously in the body. The first category includes, but is not limited to, osteoporosis, Paget's disease, hyperparathyroidism, hypercalcemia of malignancy, heterotopic ossification, and osteolytic bone metastitis. The second category includes, but is not limited to, myositis ossificans progressiva, calcinosis universalis, and such afflictions as arthritis, osteoarthritis, neuritis, bursitis, tendonitis and other inflammatory conditions which predispose involved tissue to deposition of calcium phosphates.

The terms "person at risk" and "person in need of such treatment", as used herein, mean any human or lower animal which suffers a significant risk of abnormal calcium and phosphate metabolism if left untreated, and any human or lower animal diagnosed as being afflicted with abnormal calcium and phosphate metabolism. For example, postmenopausal women; persons undergoing certain steroid therapy; persons on certain anti-convulsant drugs; persons diagnosed as having Paget's disease, hyperparathyroidism, hypercalcemia of malignancy, or osteolytic bone metastases; persons diagnosed as suffering from one or more of the various forms of osteoporosis; persons belonging to a population group known to have a significantly higher than average chance of developing osteoporosis, e.g., post-menopausal women, men over age 65, and persons being treated with drugs known to cause osteopetrosis as a side effect; persons diagnosed as suffering from myositis ossificans progressiva or calcinosis universalis; and persons afflicted with arthritis, osteoarthritis, neuritis, bursitis, tendonitis and other inflammatory conditions which predispose involved tissue to deposition of calcium phosphate.

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of diphosphonate compounds of the present invention will vary with the particular condition being treated, the age and physical condition of the patient being treated, the severity of the condition, the duration of the treatment, the nature of concurrent therapy, the specific diphosphonate employed, the particular pharmaceutically-acceptable carrier utilized, and like factors within the knowledge and expertise of the attending physician. However, single dosages can range from about 0.01 mg P to about 3500 mg P, or from about 0.0002 to about 70 mg P/kg of body weight (based on a body weight of 50 kg). Preferred single dosages are from about 1 mg P to about 600 mg P, or from about 0.02 to about 12 mg P/kg of body weight (based on a body weight of 50 kg). Up to about four single dosages per day may be administered. Daily dosages greater than about 500 mg P/kg are not required to produce the desired effect and may produce undesirable side effects. The higher dosages within this range are, of course, required in the case of oral administration because of limited absorption.

The following Examples further describe and demonstrate the preferred embodiments within the scope of the present invention. The Examples are given solely for the purpose of illustration, and are not to be construed as limitations of the present invention since many variations thereof are possible without departing from its spirit and scope.

EXAMPLE 1

Synthesis of Octahydro-1-pyrindine-6,6-diphosphonic Acid Hydrate (a) Synthesis of Dihydro-1-pyrindine-6,6-diphosphonic acid To an ice bath chilled solution of 35% potassium hydride in mineral oil (5.2 g; 0.045 moles) stirring under argon in 70 ml of DMSO (dry) is added a solution of tetraisopropylmethanediphosphonate (7.82 g; 0.023 moles) in 30 ml of DMSO. On completion of a dropwise addition, the resulting solution is stirred at room temperature for one hour. A solution of 2,3-bis(chloromethyl)pyridine (4.0 g; 0.023 mole) (crude product as isolated by K. Tsuda et. al., *Chem Pharm Bull*, 1, (1953), 142) in 15 ml of DMSO is slowly added and the reaction mixture is then heated at 90° C. for 1 hour. After cooling, the DMSO is removed under vacuum. 2.1 g (21%) of the desired product is purified via flash chromatography using a 5–15% ethanol in methylene chloride gradient on silica gel. The resulting tan oil gives the following spectral characteristics: $^1$H NMR (CDCl$_3$) 8.34 (d, 1H), 7.45 (d, 1H), 7.02 (dd, 1H), 4.77 (m, 4H), 3.58 (dt, 4H), 1.35 (d, 24H);$^{31}$P NMR (CDCl$_3$) 23.97 ppm (s).

The ester (1.92 g; 0.0043 mole) is added to 38 ml of 6N HCl, and then refluxed with stirring under an argon atmosphere for 18 hours. The resulting precipitate is filtered, rinsed with water (2×5 ml), and dried to yield 0.8 g (66.5%) of an off-white crystaline solid: mp 300° C. (dec); $^1$H NMR (D$_2$O/NaOD) 8.19 (d, 1H, J=3.4 Hz), 7.62 (d, 1H, J=7.5 Hz), 7.13 (dd, 1H, J=3,4 and 7.5 Hz), 3.46 (t, 4H, J=15.8 Hz); $^{31}$P NMR (D$_2$O/NaOD) 24.84 ppm (s).

(b) Hydrogenation to Octahydro-1-pyrindine-6,6-diphosphonic acid hydrate

Dihydro-1-pyrindine-6,6-diphosphonic acid (0.86 g, which is prepared as in part (a) hereinbefore), 70 ml of distilled H$_2$O and PtO$_2$ (0.30 g) are placed in a 500 ml Parr hydrogenation bottle. The mixture is hydrogenated at r.t. (40 psi) for 2 days. The solution is filtered and washed with hot distilled H$_2$O. The filtrate is then concentrated on a rotary evaporator. The resultant solid is then dried under vacuum overnight to give 0.75 of white crystals, mp 365° C. (dec.).

$^{31}$P NMR (D$_2$O; pH 7): P$_1$: 25.13 ppm (d, J=66 Hz); P$_2$: 25.06 ppm (d, J=67 Hz). $^{13}$C NMR (D$_2$O; p 12): 61.79 (d, N-CH), 48.6 (t, P-C-P), 45.43 (s, N-CH$_2$), 40.62, 39.91, 36.43, 24.71, 19.47 ppm. $^1$H NMR (D$_2$O; pH=7): 3.53 (1H, t, J=5.0 Hz), 3.27 (1H, d, J=14.3 Hz), 2.79 (1H, q), 2.47 (2H, m), 2.19 (3H, m), 1.27 ppm (4H, m). Anal. calc'd for C$_8$H$_{17}$NO$_6$P$_2$. H$_2$O: C, 31.69; H, 6.32; N, 4.62; Found: C, 31.85; H, 6.55; N, 4.80.

Various substituted octahydro-1-pyrindine-6,6-diphosphonic acid compounds are prepared as described hereinbefore in Example 1 by using as the starting material the appropriately substituted 2,3-bis(chloromethyl)pyridine. Such substituted starting materials may be prepared by (1) photochemically reacting substituted 2,3-dimethyl pyridine with N-chlorosuccinimide in CCl$_4$; or (2) esterifying substituted 2,3-dicarboxy pyridine with MeOH/H$^+$, followed by reduction with LiAlH$_4$, and then chlorination with SOCl$_2$. Thus, by analogous synthesis procedures the following compounds are prepared ("O-1-P-6,6-DP"=octahydro-1-pyrindine-6,6-diphosphonic acid): 2-methyl-O-1-P-6,6-DP from 6-methyl-2,3-bis(chloromethyl) pyridine; 4-ethyl-2-methyl-O-1-P-6,6-DP from 4-ethyl-6-methyl-2,3-bis-(chloromethyl) pyridine; 3-propyl-5-methyl-O-1-P-6,6-DP from 5-propyl-3-(1'-chloroethyl)-2-chloromethyl-pyridine; 4-hydroxy-O-1-P-6,6-DP from 4-hydroxy-2,3-bis(chloromethyl) pyridine; 3-ethoxy-O-1-P-6,6-DP from 5-ethoxy-2,3-bis(chloromethyl) pyridine; 3-carboxy-7-ethyl-O-1-P-6,6-DP from 5-carboxy-3-chloromethyl-2-(1'-chloropropyl) pyridine; 2-phenyl-O-1-P-6,6-DP from 6-phenyl-2,3-bis(chloromethyl) pyridine; 3-(p-methoxybenzyl)-O-1-P-6,6-DP from 5-(p-methoxybenzyl)-2,3-bis(chloromethyl) pyridine; 4-amino-O-1-P-6,6-DP from 4-nitro-2,3-bis(chloromethyl) pyridine; 4-chloro-O-1-P-6,6-DP from 4-chloro-2,3-bis(chloromethyl) pyridine; and 5-carboxy(methyl ester)-O-1-P-6,6-DP from 3-(2'-chloro-2'-acetic acid, methyl ester)-2-chloromethyl-pyridine.

EXAMPLE 2

Synthesis of Octahydro-2-pyrindine-6,6-diphosphonic Acid

Using essentially the same procedure as in Example 1(a), tetraisopropyl methane diphosphonate is converted to tetraisopropyl dihydro-2-pyrindine-6,6-diphosphonate by reaction with 3,4-bis(chloromethyl)-pyridine. The resulting ester is hydrolyzed as in Example 1(a) to yield dihydro-2-pyrindine-6,6-diphosphonic acid. The dihydro-2-pyrindine-6,6-diphosphonic acid is then converted to the octahydro-2-pyrindine-6,6-diphosphonic acid by a hydrogenation procedure which is essentially the same as in Example 1(b). Substituted octahydro-2-pyrindine-6,6-diphosphonic acid compounds are prepared as described hereinbefore in Example 1 by using as the starting material the appropriately substituted 3,4-bis(chloromethyl) pyridine.

EXAMPLE 3

Synthesis of N-methyl Octahydro-1-pyrindine-6,6-diphosphonic Acid

To a solution of tetraisopropyl dihydro-1-pyrindine-6,6-diphosphonate (0.9 g, which is prepared as in Example 1(a)) in 15 mL of ethanol is added methyl iodide (2 mL). The solution is then heated at 80°-90° overnight. The resultant salt is crystallized with ether/hexanes to yield 0.9 g of the desired methiodide salt. ($^{31}$P NMR 21.1.) The methiodide (600 mg) is then taken up in 20 mL of 6N HCl and refluxed overnight to yield 400 mg of desired methiodide acid. $^{31}$P NMR (D$_2$O; pH 11) 22.96. $^1$H NMR (D$_2$O; pH 11) 8.40(1H, d), 8.20 (1H, d), 7.66 (1H, t), 4.25(3H, s), 3.75(4H, dd).

The methiodide acid (240 mg) is taken up in 20 mL of H$_2$O and this solution is hydrogenated over PtO$_2$ (130 mg) at 50° overnight at 50 psi on a Parr Hydrogenation Apparatus. The mixture is then filtered and evaporated to yield 200 mg of desired product. $^{31}$P NMR (D$_2$O) 24.8, 24.1. $^{13}$C NMR (D$_2$O) 70.969, 70.045 (HCNH), 56.796, 43.927, 41.115, 36.022, 34.133, 23.903, 20.450 (quaternary not detected).

An analytical sample of the product is prepared by recrystallization from ethanol/water. Anal. Calc'd. for C$_9$H$_{19}$NO$_6$P$_2$.H$_2$O: C, 34.07; H, 6.67; N, 4.41. Found: C, 33:61; H, 6.53; N, 4.34.

Various N-substituted octahydro-1-pyrindine-6,6-diphosphonic acid compounds and N-substituted octahydro-2-pyrindine-6,6-diphosphonic acid compounds are prepared by an analogous synthesis procedure starting with the appropriate iodide compound. Amide containing compounds of the present invention, such as the acetylamide of octahydro-1-pyrindine-6,6-diphosphonic acid, is also prepared by a simple reaction such as between acetyl chloride and octahydro-1-pyrindine-6,6-diphosphinic acid.

EXAMPLE 4

Synthesis of Octahydro-1-pyrindine-7,7-diphosphonic acid

Synthesis of the substituted or unsubstituted octahydro-1-pyrindine-7,7-diphosphonate compounds may be achieved using a synthesis procedure analogous to the procedure for making cyano compounds disclosed in Crossley and Shepherd, *J. Chem. Soc., Perkin Trans. I*, (11), 2479–81(1985), the disclosure of which is incorporated herein by reference in its entirety. Therefore, to a 0° C. solution of cyclopentenopyridine (1 mmol) in 2 ml of THF (anhydrous) is added a pregenerated 3 ml solution of lithium diisopropyl amide (2 mmol). After stirring for 30 minutes at 0° C. under a nitrogen atmosphere, diethylchlorophosphite in 2 ml of THF is added dropwise. The reaction is stirred for 1 hr at 0° C., and then an additional hour at room temperature. The resulting mixture is quenched with saturated ammonium chloride and extracted with methylene chloride. Drying and concentration of solvent gives the crude product which is chromatographed to purity to yield tetraethyl dihydropyrindine-7,7-diphosphonate. This material is hydrolyzed and then hydrogenated by essentially the same procedures as described hereinbefore to yield octahydro-1-pyrindine-7,7-diphosphonic acid.

EXAMPLE 5

Thyroparathyroidectomized (TPTX) Rat Model

The compounds are evaluated for in vivo bone resporption inhibition potency by an animal model system known as the thyroparathyroidectomized (TPTX) rat model. The general principles of this model system are disclosed in Russell et al., *Calcif. Tissue Research*, 6, 183-196 (1970), and in Muhlbauer and Fleisch, *Mineral Electrolyte Metab.*, 5, 296-303 (1981), the disclosures of which are incorporated herein by reference. The basic biochemical concept of the TPTX system is inhibition of the parathyroid hormone (PTH)-induced rise in serum total and ionized calcium levels by the respective bone active polyphosphonates.

(a) Materials

Low calcium and low phosphorous diets used are prepared by Teklad ® Test Diets (Harlan Industries, Madison, Wis. 53711) in a pellet form of approximately 0.18% calcium and 0.22% phosphorous. The diets contain all the essential vitamins and minerals required for the rat, with the exception of calcium and phosphorous. The calcium and phosphorous levels of the pellets are verified analytically.

PTH is acquired as a powdered bovine extract (Sigma Chemical Co., P. O. Box 14508, St. Louis, Mo., order #P-4410). PTH is prepared in 0.9% saline such that the final concentration is 100 μg PTH/ml, or approximately 200 U.S.P. units/ml. All solutions are filtered through a #4 Whatman Filter Paper and refiltered through a 0.45 μm Metricel ® filter.

(b) Dose Solutions and Dosing Procedure

All solutions of compounds to be tested for bone resorption inhibition potency are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mg P/kg. Concentrations are based on dosing 0.2 ml/100 grams of body weight. Typically, all compounds are administered at 0.01, 0.1, and 1.0 mg P/kg/day for 4 days in order to determine the lowest effective dose ("LED"). Where necessary the test is repeated, whereby the animals are administered with 0.5 LED in order to refine the determination of LED. Adjustments in dosage based on changes in body weight are made on a daily basis.

(c) Animals

In this study 50 male Wistar rats weighing approximately 150-160 grams are thyroparathyroidectomized surgically by the breeder (Charles River Breeding Laboratories). All rats are double housed on arrival in suspended cages with Purina Laboratory Rodent Chow ® and tap water ad libitum. After acclimation to the laboratory environment for 3-5 days, the rats are placed on a low calcium, low phosphorous (0.18%/0.22%) diet (Teklad ®) and given 2% (W/V) calcium gluconate supplemented deionized water via water bottles.

(d) Method

On day three of low calcium diet, all rats are weighed. On day four, all rats are anesthetized with Ketaset ® (Ketamine Hydrochloride, 100 mg/ml, Bristol Myers), 0.10 ml/rat, and then bled from the retroorbital venous plexus for serum total calcium analysis using Flame Atomic Absorption (FAA) or Nova 7+7 Automated Calcium Analyzer. All rats weighing less than 150 grams are eliminated from the study. Animals are then randomized statistically such that the mean total serum calcium for each group is the same. Only rats deemed hypocalcemic (total serum calcium≦8.0 mg/dl) are placed in study groups comprising six animals per group.

Treatments with the various experimental compounds commence on day 6 and last through day 9 of the study. Dose solutions are prepared to be given at a constant rate of 0.2 ml/100 grams of body weight subcutaneously in the ventral skin flap where the hind leg meets the torso. All rats are weighed and dosed daily. A 25 gauge ⅝" needle is used to administer drug, alternating right and left dose sites daily. On day 8, animals are changed to deionized, distilled water via water bottles. On day 9 all rats are fasted in the afternoon at approximately 4:00 P.M. On day 10 of study no treatment is given. In the morning a 800 μl sample of whole blood is collected from each rat in Microtainer (B-D#5060) serum separater tubes for serum total and ionized calcium (FAA or Nova 7+7). Immediately following blood collection all rats are weighed and injected with bovin parathyroid hormone subcutaneously at a rate of 35 μg PTH per 100 grams of body weight. Blood sampling for total and ionized calcium is repeated three and one-half hours post-PTH injection.

All pre- and post-PTH total and ionized calciums from the treatment groups are statistically analyzed for significance compared to PTH alone (control) using Student's t-test, analysis of variance, and their non-parametric equivalents. The post minus pre-change and % change are also determined on calcium levels and pre-drug vs post-drug body weights.

The physiological effect of the PTH challenge is a rise in serum calcium level, with peak activity observed at three to four hours. Since the hormonal and dietary controls of calcium metabolism are minimized in the TPTX model, an observed increase in serum calcium level is presumably the result of resorption of bone material. Since polyphosphonates tend to inhibit resorption of bone materials, the animals pretreated with polyphosphonate show a rise in serum calcium level after PTH challenge which is less than that found in control animals which have been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. The LED values of the bone resorption inhibition potency of representative compounds as determined by the TPTX rat model are presented in Table 1. The data in Table 1 show that while the diphosphonic acid compounds of the present invention are potent bone resorption inhibiting agents, there are closely related cyclic diphosphonic acid compounds which are chemically very similar that either do not inhibit bone resorption or are much less potent inhibitors of bone resorption.

TABLE 1

| Lowest Effective (Antiresorptive) Dose | |
|---|---|
| Diphosphonate Compound | TPTX (mg P/kg) |
| cis-Octahydro-1-pyrindine-6,6-DP* | 0.01 |
| N-Methyl Octahydro-1-pyrindine-6,6-DP* | 1.0 |
| Dihydro-1-pyrindine-6,6-DP[5)] | N |
| Hexahydroindan-2,2-DP[5)] | 1.0 |
| Indan-2,2-DP[5)] | 0.5 |
| EHDP[1)] | 1.0 |
| APD[2)] | 0.1 |
| Cl$_2$MDP[3)] | 1.0 |
| Azacyclopentane-2,2-DP[4)] | N |

N = No activity at the highest dose level tested.
* = Compound of the present invention.
[1)]ethane-1-hydroxy-1,1-DP
[2)]3-amino propane-1-hydroxy-1,1-DP
[3)]dichloromethane DP
[4)]A compound disclosed in U.S. Pat. No. 3,988,443, issued October 26, 1976, to Ploger et al.
[5)]A compound disclosed in EPO Patent Application Publication No. 189,662; published August 6, 1986.

EXAMPLE 6

Schenk Model

The compounds are evaluated for in vivo bone resorption inhibition and mineralization inhibition in an animal model system known in the field of bone metabolism as the Schenk Model. The general principles of this model system are disclosed in Shinoda et al., *Calcif. Tissue Int.*, 35, 87-99 (1983); and in Schenk et al., *Calcif. Tissue Res.* 11, 196-214 (1973), the disclosures of which are incorporated herein by reference.

MATERIALS AND METHODS

Animals

Preweaning 17-day-old (30 gms) male Sprague Dawley rats (Charles River Breeding Laboratories) are shipped with their mothers and placed in plastic cages with their mothers upon arrival. At 19 days of age, pups receiving Rat Chow and water ad libitum are randomly allocated into treatment or control groups comprising seven animals per group. On day 1 and again on day 7 all animals are given an intraperitoneal ("IP") injection of Calcein (1% solution in 0.9% saline solution; dosed at 0.2 ml/100 g body weight). On day 4 all animals are given an IP injection of tetracycline hydrochloride (1% solution in 0.9% saline solution; dosed at 0.2 ml/100 g body weight). These compounds label actively mineralizing bone and cartilage.

Dose Solutions and Dosing Procedure

All solutions are prepared for subcutaneous injection in 0.9% normal saline and adjusted to pH 7.4 using NaOH and/or HCl. Dose solution calculation is made by considering the mass of powder (based on molecular weight, hydration) of the active material in mg/kg (body weight) that corresponds to mgP/kg. Concentrations are based on dosing 0.2 ml/100 g body weight. Typically, all compounds are administered at 0.01, 0.1, 1.0 and 10.0 mg P/kg/day for 7 days. Compounds showing activity at 0.1 mg P/kg/day are then tested at logarithmic decrements down to 0.001 mg P/kg/day. Adjustments in dosage based on changes in body weight are made on a daily basis.

Necropsy, Tissue Processing and Histomorphometry

On day 8 after the start of dosing, all animals are sacrificed by IP overdose of pentabarbitol. Tibias are dissected free and placed in 70% ethyl alcohol. One tibia is dehydrated in graded ethanol solutions and embedded in methyl methacrylate as described in Schenk, *Methods of Calcified Tissue Preparation* (G. R. Dickson, Editor; Elsevier Science Publ., The Netherlands; 1984), the disclosures of which are incorporated herein by reference in their entirety. The tibia is sectioned longitudinally through the metaphyseal area. Specimens are stained on one surface with silver nitrate and mounted on microscope slides for evaluation with a Quantimet Image Analyzer (Cambridge Instruments, Inc.) using both incandescent and ultraviolet illumination. Metaphyseal trabecular bone content is measured in the region between the fluorescent label and the growth plate: expressed as percent of total area (bone + marrow). Epiphyseal growth plate width is obtained as the mean value of 10 equally-spaced measurements across the section.

Statistical evaluation of data is made using parametric and non-parametric analysis of variance and Wilcoxons rank sum test to determine a statistically significant effect compared to control animals.

The Schenk model provides data for in vivo bone resorption inhibition by the compounds. The lowest effective (antiresorptive) dose ("LED") for representative compounds tested, as determined by the Schenk model, are provided in Table 2.

TABLE 2

| Lowest Effective (Antiresorptive) Dose - Shenk | |
|---|---|
| Diphosphonate Compound | Schenk LED (mg/P/kg) |
| EHDP[1)] | 1.0 |
| APD[2)] | 0.1 |
| Cl$_2$MDP[3)] | 1.0 |
| Cis-octahydro-1-pyrindine-6,6-DP* | 0.01 |
| Hexahydroindan-2,2-DP[4)] | 1.0 |
| Indan-2,2-DP[4)] | 1.0 |

* = Compound of the present invention.
[1)]ethane-1-hydroy-1,1-DP
[2)]3-amino propane-1-hydroxy-1,1-DP
[3)]dichloromethane DP
[4)]A compound disclosed in EPO Patent Application Publication No. 189,662; published August 6, 1986.

EXAMPLE 7

Capsules are prepared by conventional methods, comprised as follows:

| Ingredient | Mg per Capsule |
|---|---|
| Cis-Octahydro-1-pyrindine-6,6-DP | 25 (as mgP) |
| Starch | 55.60 |
| Sodium lauryl sulfate | 2.90 |

The above capsules administered orally twice daily for 6 months substantially reduce bone resorption in a patient weighing approximately 70 kilograms afflicted with osteoporosis. Similar results are obtained when cis-octahydro-1-pyrindine-6,6-DP in the above described capsules is replaced with octahydro-2-pyrindine-6,6-DP; or N-methyl-octahydro-1-pyrindine-6,6-DP; or a pharmaceutically acceptable salt or ester of these diphosphonate compounds.

EXAMPLE 8

Tablets are prepared by conventional methods, formulated as follows:

| Ingredient | Mg per tablet |
| --- | --- |
| 4-Amino-octahydro-1-pyrindine-6,6-DP | 25 (as mg P) |
| Lactose | 40 |
| Starch | 2.5 |
| Magnesium stearate | 1 |

The above tablets administered orally twice daily for 6 months substantially reduce bone resorption in a patient weighing approximately 70 kilograms afflicted with Paget's disease. Similar results are obtained when 4-amino-octahydro-1-pyrindine-6,6-DP in the above described tablets is replaced with octahydro-1-pyrindine-6,6-DP; octahydro-1-pyrindine-6,6-DP; octahydro-1-pyrindine-7,7-DP; octahydro-1-pyrindine-5,5-DP; or N-methyl-octahydro-1-pyrindine-6,6-DP; or a pharmaceutically acceptable salt or ester of these diphosphonate compounds.

EXAMPLE 9

Injectable solutions are prepared by conventional methods using 1.0 ml of physiological saline solution and 0.7 mg P of cis-octahydro-1-pyrindine-6,6-DP, adjusted to pH=7.4.

One injection, one time daily for 4 days, results in appreciable alleviation of hypercalcemia of malignancy in patients weighing approximately 70 kilograms.

EXAMPLE 10

Patients weighing approximately 70 kilograms who are clinically diagnosed as suffering from hypercalcemia of malignancy are administered 0.7 mg P of cis-octahydro-1-pyrindine-6,6-diphosphonate, or its pharmaceutically acceptable salt or ester, by a 2½ hour intravenous infusion one time daily for 4 days. This treatment results in an appreciable alleviation of the hypercalcemia of malignancy.

What is claimed is:

1. A nitrogen-containing, saturated bicyclic cyclopentane ring-containing diphosphonic acid, or a pharmaceutically-acceptable salt thereof, having one of the general structures:

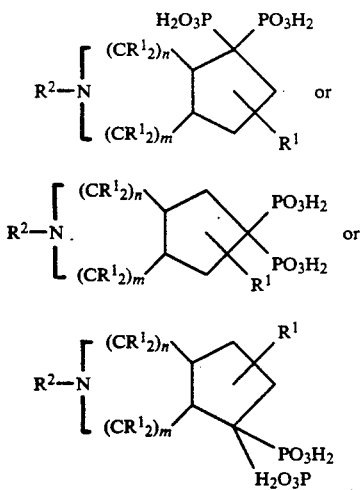

wherein m and n are integers from 0 to 3; m+n=3; each $R^1$ is independently selected from the group consisting of —$CO_2R^3$, —$O_2CR^3$, —$NR^3_2$, —$N(R^3)C(O)R^3$, —$C(O)N(R^3)_2$, —$C(O)NR^3$, phenyl, benzyl, nitro, and combinations thereof; $R^2$ is hydrogen, alkyl having from 1 to 6 carbon atoms, $R^3C(O)$, phenyl, benzyl; and each $R^3$ is independently selected from the group consisting of hydrogen and alkyl having from 1 to 3 carbon atoms.

2. A nitrogen-containing, saturated bicyclic cyclopentane ring-containing diphosphonic acid, or a pharmaceutically-acceptable salt thereof, according to claim 1, wherein said compound is an octahydro pyrindine diphosphonic acid, or salt compound selected from the group consisting of unsubstituted or substituted octahydro-1-pyrindine-5,5-diphosphonic acids; unsubstituted or substituted octahydro-1-pyrindine-6,6-diphosphonic acids; unsubstituted or substituted octahydro-2-pyrindine-6,6-diphosphonic acids; unsubstituted or substituted octahydro-1-pyrindine-7,7-diphosphonic acids; unsubstituted or substituted octahydro-2-pyrindine-7,7-diphosphonic acids; or a pharmaceutically-acceptable salt thereof.

3. An Octahydro pyrindine diphosphonic acid, or a pharmaceutically-acceptable salt thereof, according to claim 2 selected from the group consisting of substituted or unsubstituted octahydro-1-pyrindine-6,6-diphosphonic acid or salt having the following formula:

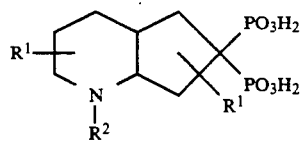

and substituted or unsubstituted octahydro-2-pyrindine-6,6-diphosphonic acid, salt having the following formula:

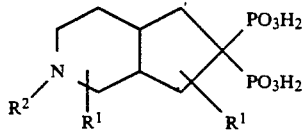

4. An Octahydro pyrindine diphosphonic acid, or a pharmaceutically-acceptable salt thereof, according to claim 3 wherein each $R^1$ is independently selected from the group consisting of —$NR^3_2$ and hydroxy; and $R^2$ is hydrogen, alkyl having from 1 to 6 carbon atoms, and $R^3C(O)$—.

5. An Octahydro-1-pyrindine-6,6-diphosphonic acid, or a pharmaceutically-acceptable salt thereof, having the following formula:

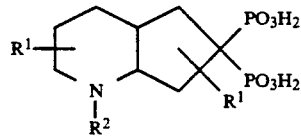

wherein each $R^1$ is independently selected from the group consisting of —$OR^3$, —$CO_2R^3$, —$O_2CR^3$, —$NR^3_2$, —$N(R^3)C(O)R^3$, —$C(O)N(R^3)_2$, —$C(O)R^3$, phenyl, benzyl, nitro, and combinations thereof; $R^2$ is hydrogen, alkyl having from 1 to 6 carbon atoms, $R^3C(O)$—, phenyl, and benzyl; and each $R^3$ is independently selected from the group consisting of hydrogen and alkyl having from 1 to 3 carbon atoms.

6. An Octahydro-1-pyrindine-6,6-diphosphonic acid, or a pharmaceutically-acceptable salt thereof, according to claim 5 wherein each $R^1$ is independently selected from the group consisting of $-NR^3_2$ and hydroxy; and $R^2$ is hydrogen, alkyl having from 1 to 6 carbon atoms, and $R^3C(O)-$.

7. An Octahydro-1-pyrindine-6,6-diphosphonic acid or a pharmaceutically-acceptable salt thereof, according to claim 6 wherein each $R^1$ is independently selected from the group consisting of $-NH_2$ and hydroxy; and $R^2$ is selected from the group consisting of hydrogen, methyl and ethyl.

8. A pharmaceutical composition comprising:
   (a) a safe and effective amount of a nitrogen-containing, saturated bicyclic cyclopentane ring-containing diphosphonic acid, salt according to claim 1; and
   (b) a pharmaceutically-acceptable carrier.

9. A pharmaceutical composition comprising:
   (a) a safe and effective amount of an octahydro pyrindine diphosphonic acid, salt according to claim 3; and
   (b) a pharmaceutically-acceptable carrier.

10. A pharmaceutical composition comprising:
    (a) a safe and effective amount of an octahydro-1-pyrindine-6,6-diphosphonic acid, salt according to claim 5; and
    (b) a pharmaceutically-acceptable carrier.

11. A pharmaceutical composition comprising:
    (a) a safe and effective amount of a an octahydro-1-pyrindine-6,6-diphosphonic acid, salt according to claim 6; and
    (b) a pharmaceutically-acceptable carrier.

12. A pharmaceutical composition comprising:
    (a) a safe and effective amount of a an octahydro-1-pyrindine-6,6-diphosphonic acid, salt according to claim 7; and
    (b) a pharmaceutically-acceptable carrier.

13. A method for treating pathological conditions characterized by abnormal calcium and phosphate metabolism in humans or lower animals, said method comprising administering to a human or lower animal in need of such treatment a safe and effective amount of a nitrogen-containing, saturated bicyclic cyclopentane ring-containing diphosphonic acid, or salt compound of claim 1.

14. A method for treating pathological conditions characterized by abnormal calcium and phosphate metabolism in humans or lower animals, said method comprising administering to a human or lower animal in need of such treatment a safe and effective amount of an octahydro-1-pyrindine-6,6-diphosphonic acid, or salt compound of claim 5.

15. A method for treating or preventing pathological conditions characterized by abnormal calcium and phosphate metabolism in humans or lower animals, said method comprising administering to a human or lower animal in need of such treatment a safe and effective amount of an octahydro-1-pyrindine-6,6-diphosphonic acid, salt or ester compound of claim 7.

* * * * *